United States Patent
Gebhardt et al.

(10) Patent No.: US 10,882,810 B2
(45) Date of Patent: Jan. 5, 2021

(54) PROCESS FOR THE PREPARATION OF SUBSTITUTED PHENOXYPHENYL ALCOHOLS

(71) Applicant: BASF Agro B.V., Arnhem (NL)

(72) Inventors: Joachim Gebhardt, Ludwigshafen (DE); Jan Klaas Lohmann, Ludwigshafen (DE); David Anderson, Germantown, MD (US); Michael Rack, Ludwigshafen (DE); Roland Goetz, Ludwigshafen (DE)

(73) Assignee: BASF AGRO B.V., Arnhem (NL)

( * ) Notice: Subject to any disclaimer, the term of this patent is extended or adjusted under 35 U.S.C. 154(b) by 0 days.

(21) Appl. No.: 16/621,655

(22) PCT Filed: Jun. 12, 2018

(86) PCT No.: PCT/EP2018/065443
§ 371 (c)(1),
(2) Date: Dec. 11, 2019

(87) PCT Pub. No.: WO2018/229027
PCT Pub. Date: Dec. 20, 2018

(65) Prior Publication Data
US 2020/0207692 A1    Jul. 2, 2020

(30) Foreign Application Priority Data
Jun. 14, 2017    (EP) .................... 17176084

(51) Int. Cl.
*C07C 41/26* (2006.01)
*C07C 43/295* (2006.01)
*C07D 249/08* (2006.01)

(52) U.S. Cl.
CPC ............ *C07C 41/26* (2013.01); *C07C 43/295* (2013.01); *C07D 249/08* (2013.01)

(58) Field of Classification Search
CPC ...... C07C 41/26; C07C 43/295; C07D 249/08
See application file for complete search history.

(56) References Cited

U.S. PATENT DOCUMENTS

| | | | | |
|---|---|---|---|---|
| 2014/0235441 A1* | 8/2014 | Dietz | .................. | A01N 43/653 504/100 |
| 2014/0243194 A1* | 8/2014 | Dietz | .................. | C07D 249/08 504/100 |
| 2018/0170848 A1 | 6/2018 | Gebhardt et al. | | |

FOREIGN PATENT DOCUMENTS

| | | |
|---|---|---|
| DE | 3042302 A1 | 8/1981 |
| WO | WO-2013/007767 A1 | 1/2013 |
| WO | WO-2014/108286 A1 | 7/2014 |
| WO | WO-2015/091045 A1 | 6/2015 |
| WO | WO-2016/005211 A1 | 1/2016 |
| WO | WO-2016/202807 A1 | 12/2016 |
| WO | WO-2017/102905 A1 | 6/2017 |

OTHER PUBLICATIONS

European Search Report for EP Patent Application No. 17176084.6, dated Nov. 23, 2017, 3 pages.
International Search Report and Written Opinion for PCT Patent Application No. PCT/EP2018/065443, dated Sep. 13, 2018.

* cited by examiner

*Primary Examiner* — Rosalynd A Keys
(74) *Attorney, Agent, or Firm* — Marshall, Gerstein & Borun LLP

(57) ABSTRACT

The present invention relates to a process for the preparation of the compounds of formula II

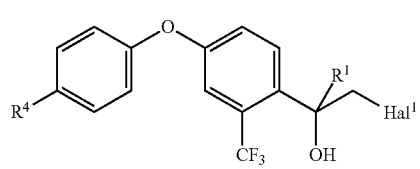

II using a lanthanoid salt.

11 Claims, No Drawings

PROCESS FOR THE PREPARATION OF SUBSTITUTED PHENOXYPHENYL ALCOHOLS

CROSS-REFERENCE TO RELATED APPLICATIONS

This application is a National Stage application of International Application No. PCT/EP2018/065443 filed Jun. 12, 2018. This application also claims priority under 35 U.S.C. § 119 to European Patent Application No. 17176084.6, filed Jun. 14, 2017.

The present invention relates to a process for providing substituted phenoxyphenyl alcohols.

Furthermore, the invention relates to the use of substituted phenoxyphenyl alcohols obtained by the inventive process for the preparation of triazoles.

The substituted phenoxyphenyl alcohols provided by the process according to the present invention are valuable intermediate compounds for the synthesis of triazole compounds having pesticidal, in particular fungicidal activity. WO 2013/007767 is directed to fungicidal substituted 1-[4-phenoxy-2-(halogenalkyl)phenyl]-2-(1,2,4-triazol-1-yl) ethanol compounds, that can be provided by using the inventive process. WO 2014/108286, WO 2015/091045 and WO2016/005211 describe processes for the synthesis of such fungicidally active triazole compounds.

The methods known from the literature are sometimes not because the yield or purity is not sufficient and/or the reaction conditions and parameters such as temperature are not optimal because they lead to unwanted side products and/or less yields. Because said substituted benzyl alcohols are valuable intermediates for the synthesis of triazole compounds with promising fungicidal activity, there is an ongoing need for alternative or improved processes that easily make such intermediates and compounds available.

An object of the present invention was to provide a process for the synthesis of substituted phenyl ketones II that are valuable intermediates for the preparation of fungicidally active triazole compounds.

Consequently, the present invention relates to a process for the preparation of alcohol compounds of formula II

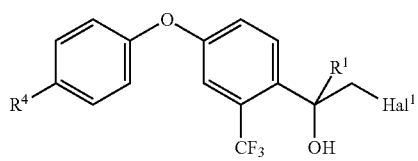

II comprising the following step:
(i) reacting a substituted phenoxy phenyl compound of the formula III

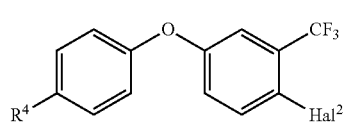

III with a Grignard reagent R'—Mg—Hal³ (IV) and a ketone R¹C(=O)CH₂Hal¹ (V) in the presence of a lanthanoid salt;

wherein the variables $R^1$, $R^4$, $Hal^1$, $Hal^2$, $Hal^3$ and R' are defined as follows:
$R^1$ is selected from $C_1$-$C_6$-alkyl and $C_3$-$C_8$-cycloalkyl;
$R^4$ is halogen; and
$Hal^1$, $Hal^2$, $Hal^3$ are independently from one another halogen; and
R' is $C_1$-$C_4$-alkyl or $C_3$-$C_6$-cycloalkyl.

In the process step (i) according to the present invention, 1-halogen-4-(4-halogen-phenoxy)-2-trifluoromethyl)benzene of the formula III, wherein $Hal^2$ is halogen, in particular Br or Cl, is used. In one specific embodiment, $Hal^2$ is Br. $R^4$ is halogen, such as F, Cl, Br, in particular F or Cl. According to one embodiment, $R^4$ is F. According to a further embodiment, $R^4$ is Cl.

The starting compounds III for the inventive process can be synthesized as known to the skilled person, in analogy to similar known syntheses or they are also partly commercially available. See for example WO 2013/007767 and the citations therein.

The compound of formula III is reacted with the Grignard reagent R'—Mg—Hal³ (IV).

R' in the Grignard reagent IV is $C_1$-$C_4$-alkyl or $C_3$-$C_6$-cycloalkyl, in particular it is selected from methyl, ethyl, isopropyl, tert-butyl, sec-butyl and cyclopropyl. Specifically, R' in the Grignard reagent is selected from isopropyl, tert-butyl, sec-butyl and cyclopropyl. In one specific embodiment, R' is isopropyl. In one further embodiment, R' is sec-butyl. $Hal^3$ stands for halogen, in particular Cl or Br. Also more than one Grignard reagent can be used in the same reaction, such as, for example reagent (IV), wherein $Hal^3$ is Br together with the respective reagent (having the same R'), wherein $Hal^3$ is Cl. According to one embodiment, $Hal^3$ is Cl and R' in the Grignard reagent is selected from isopropyl, tert-butyl, sec-butyl and cyclopropyl. According to a further embodiment, $Hal^3$ is Br and R' in the Grignard reagent is selected from isopropyl, tert-butyl, sec-butyl and cyclopropyl. In one preferred embodiment, in the inventive process, the Grignard reagent is (iso-propyl)-Mg—Cl and/or (iso-propyl)-Mg—Br, in particular (iso-propyl)-Mg—Cl or (iso-propyl)-Mg—Br. In a further embodiment, the Grignard reagent contains both, (iso-propyl)-Mg—Cl and (iso-propyl)-Mg—Br. In one further preferred embodiment, in the inventive process, the Grignard reagent is (sec-butyl)-Mg—Cl and/or (sec-butyl)-Mg—Br, in particular (sec-butyl)-Mg—Cl or (sec-butyl)-Mg—Br. In a further embodiment, the Grignard reagent contains both, (sec-butyl)-Mg—Cl and (sec-butyl)-Mg—Br.

Preferably, the Grignard reagent (IV) is used in an amount of 1 eq to 2 eq, in particular 1.1 to 1.8 eq, more specifically 1.1 to 1.6 eq, in relation to one equivalent of compound III. In particular, the amounts of 1.1 to 1.5 eq, more particularly 1.2 to 1.4 eq per mole of compound III may be favorable according to the present invention. It may be also favorable, if the amounts are 1 to 1.3 eq, more particularly 1.1 to 1.2 eq per mole of compound III. It can also be preferred if the amounts are 1.15 to 1.45 eq, in particular 1.15 to 1.35 eq per mole of compound III. Usually, the Grignard reagent is used in excess, preferably in slight excess.

When reacting the Grignard reagent IV with compound III, the Grignard reagent IV can be used as solution in an appropriate aprotic solvent such as a cyclic or acyclic ether solvent, for example tetrahydrofurane (THF), 1,4-dioxane, diethylether, 2-methyl-tetrahydrofurane and any mixture of these solvents. THF as solvent can be particularly appropriate. Typically, the Grignard reagent is added to the reaction vessel or flask containing the reagent III and a solvent.

The temperature for the reaction between the Grignard reagent IV and compound III may be from –20° C. to 70° C. and is preferably held at a maximum of 50° C., in particular at a maximum of 40° C., more preferably at a maximum of 35° C. Generally, it is preferred to have a reaction temperature of 20° C. to 45° C., in particular room temperature to 45° C., in particular 25° C. to 40° C. In a further embodiment, the temperature is 20° C. to 35° C., specifically 25° C. to 30° C.

As generally known to the skilled person, the structure of a Grignard reagent can be described by the so-called Schlenck equilibrium. A Grignard reagent undergoes a solvent-dependent equilibrium between different magnesium compounds.

According to the inventive process, step (i) is carried out in the presence of a lanthanoid salt. Usually, a lanthanoid halogenide is used, e.g. a lanthanoid chloride. In particular, a Cerium salt, more specifically a Ce(III) salt is used, such as a Cerium (III) halogenide. The lanthanoid salt can advantageously be selected from $Ce(iPrO)_3$ and $CeCl_3$, in particular $CeCl_3$. Preferably, the respective lanthanoid salt is dried properly before use. In general, when using for example $CeCl_3$ heptahydrate as starting material, it has been found to be advantageous if it is dried properly before use. Suitably, the heptahydrate was dried in an oven and converted to the monohydrate. The monohydrate was then further dried to result in anhydrous $CeCl_3$, e.g. in an oven at temperatures of about 140° C. for several hours. It has been observed that if the $CeCl_3$ was not dried properly, the yields of the desired product were lowered.

Preferably, a suitable solvent is added to the lanthanoid salt, such as Ce(III) salt, forming a lanthanoid/Ce(III) salt reaction mixture, wherein the solvent acts as complexing agent. Suitable solvents therefore are any solvents that result in good complex formation with the lanthanoid/Ce(III) salt. THF has shown to be particularly suitable for the inventive process.

Preferably, the lanthanoid salt is used in an amount of 0.1 eq to 5 eq, in particular 0.2 to 3 eq, more specifically 0.3 to 2.5 eq, in relation to one equivalent of compound III. In particular, the amounts of 0.4 to 2 eq, more particularly 0.4 to 1.5 eq per mole of compound III may be favorable according to the present invention. It may be also favorable, if the amounts are 0.5 to 1.3 eq, more specifically 0.6 to 1.2 eq. Usually, the lanthanoid salt is used in excess, preferably in slight excess.

One appropriate course of reaction is such that the Grignard reagent (IV) is first reacted with the compound of formula III and then, this reaction mixture is added to the lanthanoid/Ce(III) salt reaction mixture. Then, a solution of reagent (V) is added dropwise.

When combining the reaction mixture and the lanthanoid salt, the temperature is usually held at –50° C. to 30° C., and it is preferably held at a maximum of 20° C., in particular at a maximum of 0° C., more preferably at a maximum of –5° C. In may be preferred to hold the reaction mixture at a maximum of –10° C., more specifically at a maximum of –15°. Generally, a reaction temperature of –20° C. to 30° C. is preferred. In a further embodiment, the temperature is 20° C. to 35° C., specifically 25° C. to 30° C.

$R^1$ in the ketone $R^1C(=O)CH_2Hal^1$ (V) as well as in the other compounds containing this variable, is $C_1$-$C_6$-alkyl or $C_3$-$C_8$-cycloalkyl, in particular selected from $CH_3$, $CH(CH_3)_2$ and cyclopropyl.

According to one embodiment, $R^1$ is $C_1$-$C_6$-alkyl, more specifically $C_1$-$C_4$-alkyl, in particular selected from $CH_3$, $C_2H_5$, n-$C_3H_7$, $CH(CH_3)_2$, n-butyl, iso-butyl and tert-butyl, more particularly selected from $CH_3$, $C_2H_5$, $CH(CH_3)_2$ and $C(CH_3)_3$, even more particularly $CH_3$ or $CH(CH_3)_2$. In one particularly preferred embodiment, $R^1$ is $CH_3$. In a further embodiment, $R^1$ is $CH(CH_3)_2$.

According to still a further embodiment, $R^1$ is $C_3$-$C_8$-cycloalkyl, in particular $C_3$-$C_6$-cycloalkyl, such as $C_3H_5$ (cyclopropyl), $C_4H_7$ (cyclobutyl), cyclopentyl or cyclohexyl. A further embodiment relates to compounds, wherein $R^1$ is $C_3H_5$ (cyclopropyl) or $C_4H_7$ (cyclobutyl), more specifically cyclopropyl.

$Hal1$ in compounds (V) as well as in the compounds II, is halogen such as F, Cl, Br, in particular Br or Cl. According to one particular embodiment $Hal^1$ is Cl.

The ketone $R^1C(=O)CH_2Hal^1$ (V) is preferably used in an equimolar amount or in excess compared to the reagent of formula III. Specifically, the ketone (V) is used in an amount of 1 eq to 3 eq, in particular 1.1 to 2.8 eq, more specifically 1.2 to 2.5 eq, in relation to one equivalent of compound III. In particular, the amounts of 1.3 to 2.2 eq, more specifically 1.4 to 2.0 eq per mole of compound III may be favorable according to the present invention. Usually, the ketone (V) is used in excess, preferably in slight excess.

Preferably, the temperature range for the reaction with reagent $R^1C(=O)CH_2Hal^1$ (V) is –30° C. to 30° C. In particular, according to a specific embodiment of the present invention, the temperature is held at –15° C. to 20° C., more specifically at –15° C. to 5° C.

Appropriate solvents used in step (i) of the inventive process are aprotic organic solvents. Examples are diethylether, tetrahydrofurane (THF), methyl-tert-butylether (MTBE), 2-methyl-tetra-hydrofurane, 1,4-dioxane, 3,4-dihydro-2H-pyrane, 1,2-dimethoxyethane, tetrahydropyrane, furane, diisopropylether, toluene, ortho-xylene, meta-xylene, para-xylene and/or mesitylene, and any mixtures thereof. It can be advantageous, if the aprotic organic solvent is a cyclic or acyclic ether, such as for example THF, or toluene or any mixture thereof.

According to one particular embodiment, in step (i) a cyclic or acyclic ether solvent is used, such as for example diethylether, tetrahydrofurane (THF), methyl-tert-butylether (MTBE), 2-methyl-metrahydrofurane, 1,4-dioxane, 3,4-dihydro-2H-pyrane, 1,2-dimethoxyethane, tetrahydropyrane, furane and any mixtures thereof, in particular THF.

After step (i), a work-up of the reaction mixture can be carried out by procedures known to the person skilled in the art.

The raw product obtained after the work-up can be directly used in a further process step, e.g. step (ii) as described in the following. However, the raw product can also be further worked up and/or purified as generally known to the skilled person. If this is deemed appropriate, the reaction mixture is extracted with a suitable organic solvent (for example aromatic hydrocarbons such as toluene and xylenes) and the residue is, if appropriate, purified by recrystallization and/or chromatography.

According to the present invention, it was found that the lanthanoid mediated alkylation, in particular using a Ce-salt such as $CeCl_3$, results in higher yields of the desired product compared to similar reaction conditions not using $CeCl_3$. THF used as a solvent and/or complexing agent for the lanthanoid salt was found to be particularly suitable and generally resulted in very good yields of the desired product.

The inventive process leads to compounds II that are valuable intermediates for the synthesis of fungicidal triazole compounds. In the following, a possible synthesis route to such fungicides using said intermediates II is described.

For example, according to the present invention, the fungicide mefentrifluconazole ((2RS)-2-[4-(4-chlorophenoxy)-α,α,α-trifluoro-o-tolyl]-1-(1H-1,2,4-triazol-1-yl)propan-2-ol) can be synthesized.

Consequently, the present invention also relates to a process for the preparation of triazole compounds of the formula I,

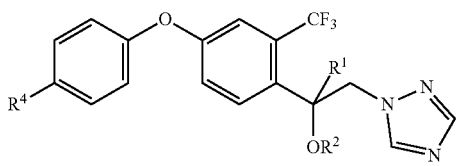

comprising the following steps:
(i) reacting a substituted phenoxy phenyl compound of the formula III

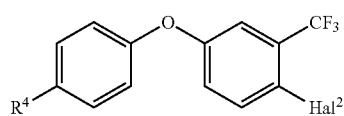

with a Grignard reagent R'—Mg—Hal$^3$ (IV) and a ketone R$^1$C(=O)CH$_2$Hal$^1$ (V) in the presence of a lanthanoid salt;
wherein the variables R$^1$, R$^4$, Hal$^1$, Hal$^2$, Hal$^3$ and R' are defined as follows:
R$^1$ is selected from C$_1$-C$_6$-alkyl and C$_3$-C$_8$-cycloalkyl;
R$^4$ is halogen; and
Hal$^1$, Hal$^2$, Hal$^3$ are independently from one another halogen; and
R' is C$_1$-C$_4$-alkyl or C$_3$-C$_6$-cycloalkyl. and
(ii) reacting the compound of the formula II resulting from step (i) with 1H-1,2,4-triazole in the presence of a base to obtain compounds I, wherein R$^2$ is hydrogen (compounds I-1)

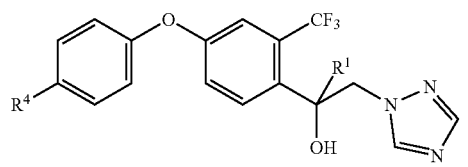

and, for obtaining compounds, wherein R$^2$ is different from hydrogen (compounds I-2):
(iii) derivatizing the compound of formula (I-1) as defined in step (ii) under basic conditions with R$^2$-LG, wherein LG is a nucleophilically replaceable leaving group; to result in compounds (I-2); wherein
R$^2$ is hydrogen, C$_1$-C$_6$-alkyl, C$_2$-C$_6$-alkenyl or C$_2$-C$_6$-alkynyl; and wherein the aliphatic moieties of R$^2$ are not further substituted or do carry one, two, three or up to the maximum possible number of identical or different groups R$^{12a}$, which are independently selected from halogen, OH, CN, nitro, C$_1$-C$_4$-alkoxy, C$_3$-C$_8$-cycloalkyl, C$_3$-C$_8$-halocycloalkyl and C$_1$-C$_4$-halogenalkoxy.

LG represents a nucleophilically replaceable leaving group such as halogen, alkylsulfonyl, alkyl-sulfonyloxy and arylsulfonyloxy, preferably chloro, bromo or iodo, particularly preferably bromo.

According to one embodiment, R$^2$ is C$_1$-C$_6$-alkyl, in particular C$_1$-C$_4$-alkyl, such as CH$_3$, C$_2$H$_5$, CH(CH$_3$)$_2$, CH$_2$CH$_2$CH$_3$, CH$_2$CH$_2$CH$_2$CH$_3$, CH$_2$CH(CH$_3$)$_2$. A further embodiment relates to compounds, wherein R$^2$ is C$_2$-C$_6$-alkyl, in particular C$_2$-C$_4$-alkyl, that is substituted by one, two or three or up to the maximum possible number of identical or different groups R$^{12}$a, as defined and preferably defined herein.

According to another embodiment, R$^2$ is C$_2$-C$_6$-alkenyl, in particular C$_2$-C$_4$-alkenyl, such as CH$_2$CH=CH$_2$, CH$_2$C(CH$_3$)=CH$_2$ or CH$_2$CH=CHCH$_3$. A further embodiment relates to compounds, wherein R$^2$ is C$_2$-C$_6$-alkenyl, in particular C$_2$-C$_4$-alkenyl, that is substituted by one, two or three or up to the maximum possible number of identical or different groups R$^{12a}$ as defined and preferably defined herein.

According to still another embodiment, R$^2$ is C$_3$-C$_8$-cycloalkyl, in particular C$_3$-C$_6$-cycloalkyl, such as C$_3$H$_5$ (cyclopropyl), C$_4$H$_7$ (cyclobutyl), cyclopentyl or cyclohexyl. A further embodiment relates to compounds, wherein R$^2$ is C$_3$-C$_8$-cycloalkyl, in particular C$_3$-C$_6$-cycloalkyl, such as C$_3$H$_5$ (cyclopropyl) or C$_4$H$_7$ (cyclobutyl), that is substituted by one, two, three four or five or up to the maximum possible number of identical or different groups R$^{12b}$ as defined and preferably defined herein.

R$^{12}$a according to the invention is preferably independently selected from F, Cl, OH, CN, C$_1$-C$_2$-alkoxy, cyclopropyl, 1-F-cyclopropyl, 1-Cl-cyclopropyl and C$_1$-C$_2$-halogenalkoxy.

In one embodiment of the invention, in the process step (ii) an inorganic base is used.

Preferably, the base used in step (ii) is selected from NaOH, KOH, Na$_2$CO$_3$ and K$_2$CO$_3$, more specifically from NaOH and KOH. According to one embodiment, NaOH is used. According to a further embodiment, KOH is used.

According to a specific embodiment, the sodium salt of 1H-1,2,4-triazole as a base is used, wherein said sodium salt is prepared using triazole and a base preferably selected from NaOH, NaH and Na-alcoholates. See also DE 3042302.

The amount of base used in step (ii) is preferably equal to or less than 2 eq, in particular less than 1.5 eq, more preferably equal to or less than 0.8 eq, even more preferably equal to or less than 0.6 equivalents per 1 equivalent of compound II. Also preferred are amounts of base being equal to or less than 0.4 equivalents, in particular equal to or less than 0.2 equivalents, specifically equal to or less than 0.1 eq per 1 equivalent of compound II. Preferably, at least 0.1 eq, more preferably at least 0.2 equivalents, in particular at least 0.3, more specifically at least 0.4 eq, even more specifically at least 0.5 eq base per 1 equivalent of compound II are used.

It may be favorable, if, in the synthesis of compounds I, less than 1 eq of base is used in relation to compound II. In specific embodiments thereof, NaOH is used as a base, preferably in an amount as given above, in particular in an amount of 0.1 to 0.55 eq in relation to compound II.

In order to have preferred reaction times, temperatures of at least 100° C., more preferably at least 110° C., in particular at least 120° C. are favorable. It is also an embodiment to reflux the reaction mixture. Preferably, the reaction temperature is not higher than 150° C., in particular not higher than 140° C. Specifically, a reaction temperature of 110° C. to 130° C. is used.

The amount of 1H-1,2,4-triazole used in step (ii) is generally at least 1 eq per mole of compound II. According to one embodiment, the 1H-1,2,4-triazole is used in excess in relation to the oxirane II. It may be preferred to use more than 1 eq to 2 eq, more specifically more than 1 eq to 1.8 eq, even more specifically more than 1 eq to 1.6 eq. Mostly for economic reason, it can be preferred to use at least 1.1 eq, specifically 1.15 eq, to 1.5 eq of triazole in relation to comound II.

Examples for appropriate solvents for step (ii) of the inventive process are aprotic organic solvents such as for example dimethyl formamide (DMF), N-methyl pyrrolidone (NMP), Dimethyl imidazolidinone (DMI), toluene, o-xylene, dimethylacetamide (DMA) and any mixtures thereof. According to one embodiment, DMF, DMA, toluene and NMP or any mixtures thereof, are used. According to a specific embodiment, the solvent used in step (ii) is selected from DMF, DMA and NMP, in particular the solvent is DMF.

In one embodiment of the invention, the product resulting from step (ii) or (iii), respectively, is crystallized from toluene and/or ortho-xylene and/or an aliphatic alcohol and/or carbonic acid ester and/or a dipolar aprotic solvent. According to one embodiment, aliphatic alcohol solvents for the crystallization of the product resulting from step (ii) or (iii) can be selected from methanol, ethanol, n-propanol, iso-propanol, n-butanol, isobutanol and any mixture thereof. According to one embodiment, n-butyl acetate or ethyl acetate or any mixture thereof is used for crystallization of the product resulting from step (ii) or (iii). According to a specific embodiment, the dipolar aprotic solvent can be selected from DMF, NMP, and dimethylacetamide.

In one embodiment, in the compound of formula I, $R^2$ is H, $R^1$ is $CH_3$ and $R^4$ is Cl.

Generally, the symmetric triazole I' is an undesired side product in the synthesis of compounds I (I-1') that may occur.

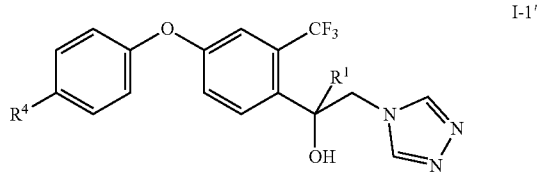

I-1' wherein $R^1$ and $R^4$ are defined and preferably defined above.

At least some of the compounds of formula II are novel and are also an object of the present invention. Consequently, the present invention also relates to novel compounds of formula II

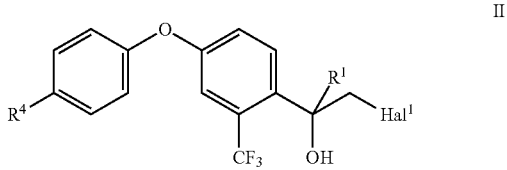

II

Wherein $R^1$, $R^4$ and $Hal^1$ are as defined and preferably defined herein.

In particular, the present invention relates to compounds IIA and IIB, wherein $R^1$, $R^4$ and $Hal^1$ are as defined and preferably defined herein:

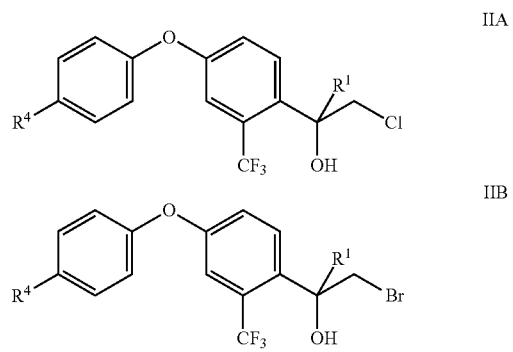

Particularly, the present invention relates to compounds IIA and IIB individualized in the following:

Compound IIA-1 The compound formula IIA, wherein $R^1$ is $CH_3$ and $R^4$ is Cl.
Compound IIA-2 The compound formula IIA, wherein $R^1$ is $CH(CH_3)_2$ and $R^4$ is Cl.
Compound IIA-3 The compound formula IIA, wherein $R^1$ is cyclopropyl and $R^4$ is Cl.
Compound IIA-4 The compound formula IIA, wherein $R^1$ is $CH_3$ and $R^4$ is F.
Compound IIA-5 The compound formula IIA, wherein $R^1$ is $CH(CH_3)_2$ and $R^4$ is F.
Compound IIA-6 The compound formula IIA, wherein $R^1$ is cyclopropyl and $R^4$ is F.
Compound IIB-1 The compound formula IIB, wherein $R^1$ is $CH_3$ and $R^4$ is Cl.
Compound IIB-2 The compound formula IIB, wherein $R^1$ is $CH(CH_3)_2$ and $R^4$ is Cl.
Compound IIB-3 The compound formula IIB, wherein $R^1$ is cyclopropyl and $R^4$ is Cl.
Compound IIB-4 The compound formula IIB, wherein $R^1$ is $CH_3$ and $R^4$ is F.
Compound IIB-5 The compound formula IIB, wherein $R^1$ is $CH(CH_3)_2$ and $R^4$ is F.
Compound IIB-6 The compound formula IIB, wherein $R^1$ is cyclopropyl and $R^4$ is F.

EXAMPLES

The following examples further illustrate the present invention and do not restrict the invention in any manner.

Example 1: Synthesis of Compound I-1, Wherein $R^1$ is $CH_3$ and $R^4$ is Cl $CeCl_3*7H_2O$ (100 g, 268 mmol) was dried in a vacuum oven at 80° C. with a $N_2$ sweep for 8 h and subsequently dried at 100° C. with a $N_2$ sweep for 12 h. The material was determined to be $CeCl_3*H_2O$ based on weight loss. The material was pulverized in a mortis and pestle and stored in an air tight glass flask. $CeCl_3*H_2O$ (14 g, 53 mmol) was transferred to a jacketed 250 mL flask and dried at 140° C. with a $N_2$ sweep for 36 h. The reactor was cooled to 40° C. followed by the addition of THF (100 mL). After stirring for 2 h, the reaction was cooled to −15° C. Under $N_2$, compound III, wherein $Hal^2$ is Br and $R^4$ is Cl (17.7 g, 99%, 50 mmol) was dissolved into THF (50 mL, 2M) and warmed to 30° C.

i-PrMgCl (30 mL, 2 M, 60 mmol) was added dropwise and the mixture was stirred for an additional 1 h. HPLC analysis verified the consumption of the bromide educt. This solution was added dropwise to the CeCl₃ mixture at −15° C. After addition, the mixture was warmed to 0° C. and stirred for 1 hr. The reaction was cooled to −15° C. Chloroacetone (8.5 g, 96%, 96 mmol) in THF (50 mL, 2 M) was added dropwise. The mixture was allowed to warm to 0° C. and stir for 1 hr. The reaction was quenched with H₂O (2 g) and allowed to warm to room temperature. The crude material was distilled under reduced pressure at 40° C. to remove THF. MTBE (100 g) was added and the slurry was filtered. The solids were washed twice with MTBE (2×50 g). Solvents were removed under reduced pressure providing compound II, wherein $Hal^1$ is Cl, $R^1$ is $CH_3$ and $R^4$ is Cl, as a clear oil. The alcohol (31 mmol) was dissolved into DMF (30 mL, 1M). 1,2,4-triazole (2.8 g, 40 mmol) and NaOH (3 g, 76 mmol) were added. The reaction was warmed to 125° C. and monitored by HPLC. HPLC analysis of the crude product indicated a 1:10 ratio of symmetrical isomer I' to the desired end product I (mefentrifluconazole). The yield of the desired product was 74.7%.

Example 2: Synthesis of Compound II Wherein $Hal^1$ is Cl, $R^1$ is $CH_3$ and $R^4$ is Cl As explained in Example 1 but using 1.1 eq of CeCl₃ instead of 0.5 eq CeCl₃ and adding the Grignard to the CeCl₃ mixture at −20 instead of −15° C. After the addition of the chloroacetone, the mixture was allowed to warm to 0° C. and stirred for 1 hr, then it was stirred another 12 h at 22° C. The ratio of the desired product to the side product 1-(4-chlorophenoxz)-3-(trifluorome-thyl)benzene (also called side-product "B") was 78:22.

Example 3: Synthesis of Compound II Wherein $Hal^1$ is Cl, $R^1$ is $CH_3$ and $R^4$ is Cl As explained in Example 1 but using 1.1 eq of CeCl₃ instead of 0.5 eq CeCl₃ and drying it at 140° C. with a N₂ sweep for 60 h. The ratio of the desired product to the side product "B" was 75:25.

Example 4: Synthesis of Compound II Wherein $Hal^1$ is Cl, $R^1$ is $CH_3$ and $R^4$ is Cl As explained in Example 1 but using 1.1 eq of CeCl₃ instead of 0.5 eq CeCl₃ and drying it at 140° C. with a N₂ sweep for 60 h. After the addition of the chloroacetone, the mixture was allowed to warm to 0° C. and stir for 1 hr, then it was allowed to stirred another 3 days at 5° C. The ratio of the desired product to the side product "B" was 80:20.

Comparison Example 1: Synthesis of Compound II Wherein $Hal^1$ is Cl, $R^1$ is $CH_3$ and $R^4$ is Cl, not Using Any Lanthanoid Salt The example as carried out in analogy to Example 1, but no lanthanoid salt was used. Also, in the reaction with iPrMgCl, THF and toluene were used as solvents, and the chloroacetone was added as solution in toluene. The reaction resulted in a yield of around 6% of the desired compound II.

The invention claimed is:
1. A process for the preparation of the compounds of formula II

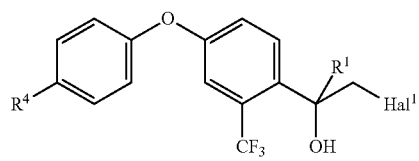

comprising the following step:
(i) reacting a substituted phenoxy phenyl compound of the formula III

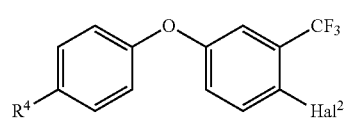

with a Grignard reagent R'—Mg-$Hal^3$ (IV) and a ketone $R^1C(\!=\!O)CH_2Hal^1$ (V) in the presence of a lanthanoid salt;
wherein the variables $R^1$, $R^4$, $Hal^1$, $Hal^2$, $Hal^3$ and R' are defined as follows:
R1 is selected from $C_1$-$C_6$-alkyl and $C_3$-$C_8$-cycloalkyl;
R4 is halogen; and
$Hal^1$, $Hal^2$, $Hal^3$ are independently from one another halogen; and
R' is $C_1$-$C_4$-alkyl or $C_3$-$C_6$-cycloalkyl.
2. The process of claim 1, wherein the lanthanoid salt is a Cerium (III) salt.
3. The process of claim 2, wherein the Cerium (III) salt is CeCl₃ or Ce(iPrO)₃.
4. The process of claim 1, wherein the reacting in step (i) comprises reacting in a solvent comprising tetrahydrofuran (THF).
5. An intermediate compound of formula II according to claim 1.
6. A process for the preparation of the compounds of formula I

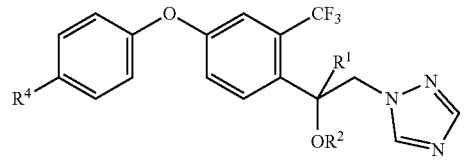

comprising the following steps:
(i) preparing a compound II according to claim 1;
(ii) reacting the compound of the formula II resulting from step (i) with 1H-1,2,4-triazole in the presence of a base to obtain compounds I, wherein $R^2$ is hydrogen (compounds I-1)

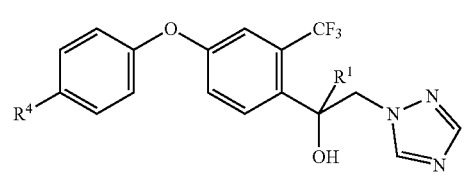

and, for obtaining compounds, wherein $R^2$ is different from hydrogen (compounds I-2):

(iii) derivatizing the compound of formula (I-1) as defined in step (ii) under basic conditions with $R^2$-LG, wherein LG is a nucleophilically replaceable leaving group; to result in compounds (I-2);

wherein the variables $R^1$ and $R^4$ are defined in claim 1, and $R^2$ is hydrogen, $C_1$-$C_6$-alkyl, $C_2$-$C_6$-alkenyl or $C_2$-$C_6$-alkynyl;

wherein the aliphatic moieties of $R^2$ are not further substituted or do carry one, two, three or up to the maximum possible number of identical or different groups $R^{12a}$ which independently are selected from halogen, OH, CN, nitro, $C_1$-$C_4$-alkoxy, $C_3$-$C_8$-cycloalkyl, $C_3$-$C_8$-halocycloalkyl and $C_1$-$C_4$-halogenalkoxy.

7. The process of claim 6, wherein the product resulting from step (ii) or (iii), respectively, is crystallized from toluene and/or ortho-xylene and/or an aliphatic alcohol and/or carbonic acid ester and/or a dipolar aprotic solvent.

8. The process of claim 7, wherein the aliphatic alcohol is selected from methanol, ethanol, n-propanol, iso-propanol, n-butanol, isobutanol and any mixture thereof.

9. The process of claim 7, wherein n-butyl acetate or ethyl acetate or any mixture thereof is used for crystallization.

10. The process of claim 7, wherein the dipolar aprotic solvent is selected from DMF, NMP, and dimethylacetamide.

11. The process of claim 6, wherein $R^2$ is H, $R^1$ is $CH_3$ and $R^4$ is Cl.

\* \* \* \* \*